US011414388B2

(12) United States Patent
Niu et al.

(10) Patent No.: US 11,414,388 B2
(45) Date of Patent: Aug. 16, 2022

(54) CRYSTAL FORM OF 3-(4-METHYL-1H-IMIDAZOL-1-YL)-5-TRIFLUOROMETHYLANILINE MONOHYDROCHLORIDE AND USE THEREOF

(71) Applicants: ARIZEST (SHANGHAI) PHARMATECH CO., LTD., Shanghai (CN); JIANGSU XIDI PHARMACEUTICALS CO., LTD., Jiangsu (CN); SHANGHAI ACEBRIGHT PHARMACEUTICALS GROUP CO., LTD., Shanghai (CN)

(72) Inventors: Deliang Niu, Shanghai (CN); Bojun Ma, Shanghai (CN); Zhanqun Zhu, Shanghai (CN); Qiang Wan, Shanghai (CN)

(73) Assignees: Arizest (Shanghai) Pharmatech Co., Ltd., Shanghai (CN); Jiangsu Xidi Pharmaceuticals Co., Ltd., Jiangsu (CN); Shanghai Acebright Pharmaceuticals Group Co., Ltd., Shanghai (CN)

( * ) Notice: Subject to any disclaimer, the term of this patent is extended or adjusted under 35 U.S.C. 154(b) by 153 days.

(21) Appl. No.: 17/046,575

(22) PCT Filed: Apr. 8, 2019

(86) PCT No.: PCT/CN2019/081771

§ 371 (c)(1),
(2) Date: Oct. 9, 2020

(87) PCT Pub. No.: WO2019/196802

PCT Pub. Date: Oct. 17, 2019

(65) Prior Publication Data

US 2021/0139433 A1 May 13, 2021

(30) Foreign Application Priority Data

Apr. 10, 2018 (CN) ........................ 201810316286.2

(51) Int. Cl.

*C07D 233/00* (2006.01)
*C07D 401/14* (2006.01)
*C07D 233/58* (2006.01)

(52) U.S. Cl.

CPC ......... *C07D 233/58* (2013.01); *C07D 401/14* (2013.01); *C07B 2200/13* (2013.01)

(58) Field of Classification Search

CPC ................ C07D 233/58; C07D 401/14; C07B 2200/13

See application file for complete search history.

(56) References Cited

U.S. PATENT DOCUMENTS 7,169,791 B2 1/2007 Breitenstein et al.

FOREIGN PATENT DOCUMENTS

| | | | |
|---|---|---|---|
| CN | 101045727 | A | 10/2007 |
| CN | 101189212 | A | 5/2008 |
| CN | 102180836 | A | 9/2011 |
| CN | 102321073 | A | 1/2012 |
| WO | 2006135619 | A1 | 12/2006 |
| WO | 2006135640 | A2 | 12/2006 |
| WO | 2010009402 | A2 | 1/2010 |

*Primary Examiner* — Sikarl A Witherspoon
(74) *Attorney, Agent, or Firm* — Ice Miller LLP

(57) ABSTRACT

The present invention relates to a crystal form of 3-(4-methyl-1H-imidazol-1-yl)-5-trifluoromethylaniline monohydrochloride and the use thereof. Specifically, disclosed are a crystal form A of a monohydrochloride anhydrous substance of 3-(4-methyl-1H-imidazol-1-yl)-5-trifluoromethylaniline monohydrochloride, a method for preparing the crystal form A and the use of the crystal form in the synthesis of nilotinib. The crystal form A of the present invention has good stability and purity, and can be directly used in the preparation and production of nilotinib. The method for preparing nilotinib in the present invention is easy to operate and has high industrial application value.

10 Claims, 1 Drawing Sheet

CRYSTAL FORM OF 3-(4-METHYL-1H-IMIDAZOL-1-YL)-5-TRIFLUOROMETHYLANILINE MONOHYDROCHLORIDE AND USE THEREOF

CROSS-REFERENCE TO RELATED APPLICATION

This application is a Section 371 of International Application No. PCT/CN2019/081771 filed Apr. 8, 2019, which was published in the Chinese language Oct. 17, 2019, under International Publication No. WO 2019/196802 A1, which claims priority under 35 U.S.C. § 119(b) to Chinese Patent Application No. 201810316286.2 filed Apr. 10, 2018, the disclosures of which are incorporated herein by reference in their entireties.

FIELD OF INVENTION

The invention relates to the field of pharmaceutical chemistry, in particular, a crystal form of a monohydrochloride anhydrous substance of 3-(4-methyl-1H-imidazol-1-yl)-5-trifluoromethylaniline (which is an intermediate of tyrosine kinase inhibitor nilotinib), and the preparation method and use thereof.

BACKGROUND

Nilotinib (trade name: Tasigna) is a highly selective tyrosine kinase inhibitor that is clinically used for treating Gleevec (imatinib) resistant Philadelphia chromosome-positive adult chronic mydogenous leukemia which is chronic or in acceleration period.

U.S. Pat. No. 7,169,791 first discloses the chemical structure of nilotinib (Formula II) and its medicinal use for inhibiting activity of the protein tyrosine kinase (TK) of bcr-abl.

(II)

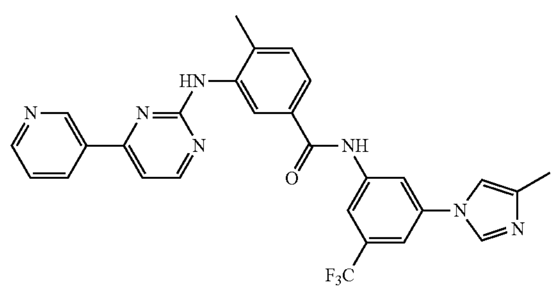

U.S. Pat. No. 7,169,791 further discloses the synthesis method of nilotinib.

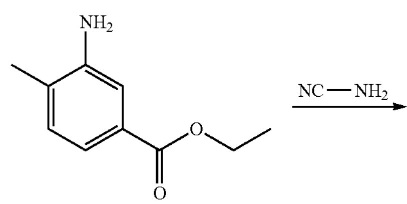

-continued

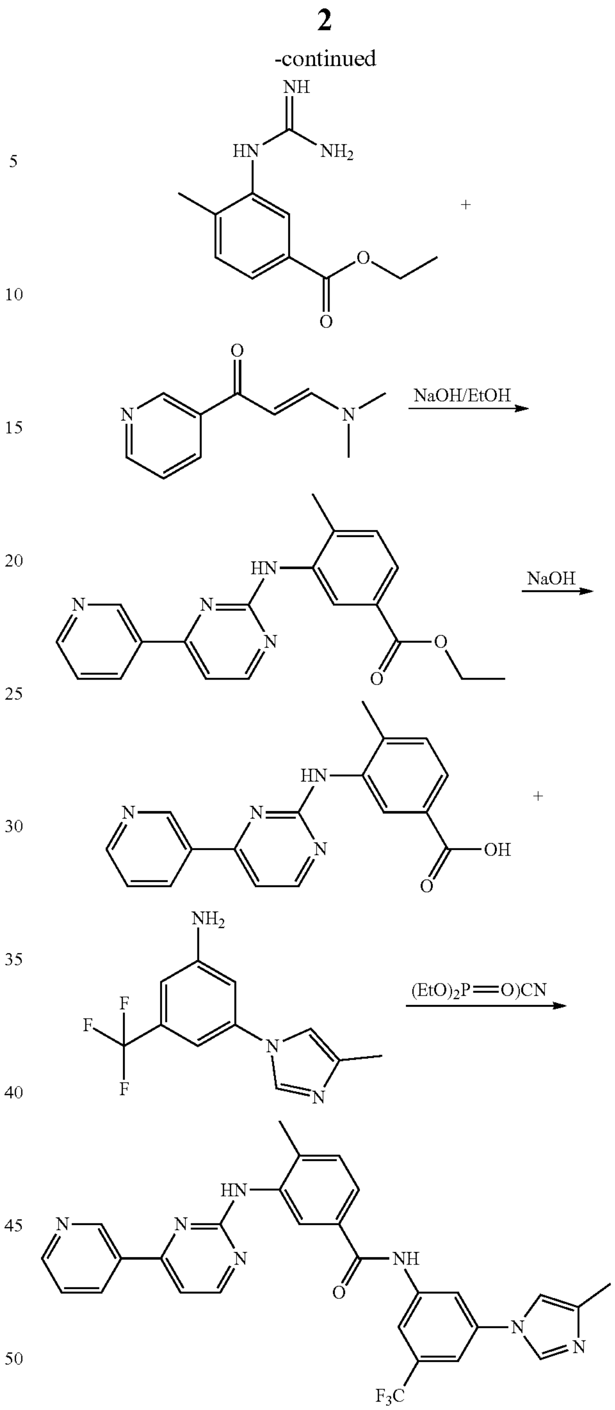

U.S. Pat. No. 7,169,791 further describes the preparation method of 3-(4-methyl-1H-imidazol-1-yl)-5-trifluoromethylaniline (hereinafter referred to Niloamine), which is the key intermediate of nilotinib. According to this patent, the preparation of the intermediate is achieved by a 4-step synthesis scheme, in which the last step is the removal of amino acid protecting group by using hydrochloric acid. After the completion of the reaction, a reaction solution containing the compound of formula (I) is obtained. Without isolation, to the reaction solution is added inorganic alkali aqueous to free the compound of formula (I) in order to obtain niloamine free base, which participates in the synthesis of nilotinib in the form of niloamine free base.

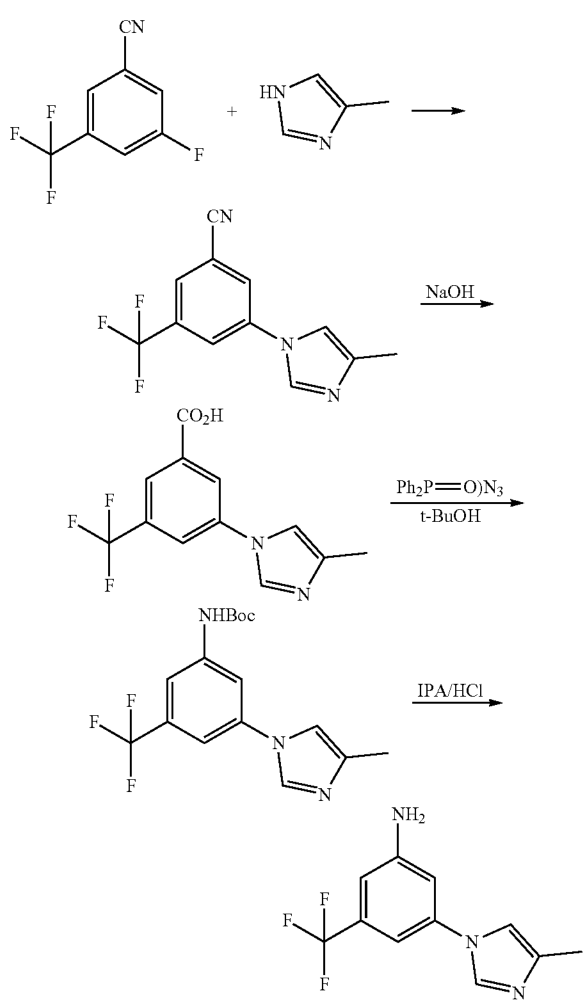

WO2006/135640 reported that the current method for the industrial preparation of intermediate niloamine: 1-bromo-3-nitro-5-trifluoromethylbenzene, which is used as the starting material, is reduced to 3-bromo-5-trifluoromethylaniline by Pd/C hydrogenation, then coupled with 4-methyl-1H-imidazole and recrystallized.

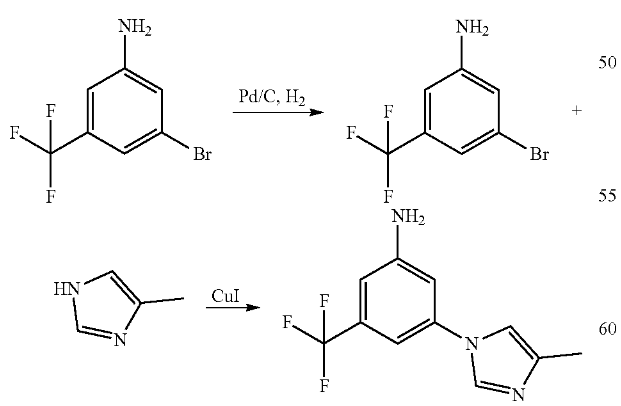

WO2006/135619 reported a synthesis method wherein 1,3-dinitro-5-trifluoromethylbenzene, which is used as the starting material, is firstly reacted with 4-methyl-1H-imidazole to obtain 4-methyl-1-(3-nitro-5-(trifluoromethyl)phenyl)-1H-imidazole, and then the nitro group is hydrogenation reduced to obtain nilotamine. Meanwhile, methanol/acetone and toluene/acetone were respectively used as solvent in Example 2 and Example 3 of the patent in order to purify the intermediate, concentrated hydrochloric acid was added to salify and cooled to crystallize. The wet products obtained by filtration were directly dissolved in the hot methanol without drying, and recrystallized by adding alkali in order to remove impurities in the reaction. In this reaction, a qualified product can only be obtained by salinization, neutralization, and recrystallization with the free base, which is somewhat cumbersome.

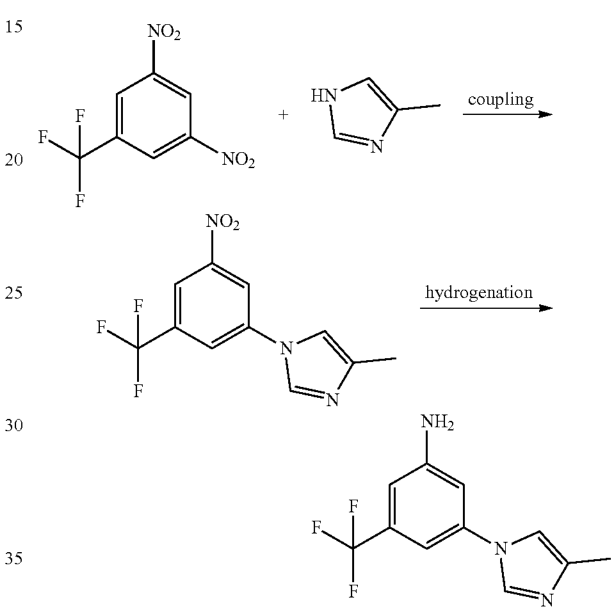

Therefore, there is still a need in the art for a method for preparing nilotinib with simple operation and lower cost.

SUMMARY OF THE INVENTION

The purpose of the present invention is to provide a method for preparing nilotinib with simple operation and lower cost.

The further purpose of the present invention is to provide a new crystal form of niloamine hydrochloride, an intermediate for preparing nilotinib, and the preparation method thereof.

In the first aspect of the present invention, crystal form A of the compound of formula (I) is provided, of which the X-ray powder diffraction pattern has 2θ value characteristic peaks at of 8.43±0.2°, 12.59±0.2°, 16.95±0.2°, 22.46±0.2°, 25.76±0.2°, and 26.48±0.2°;

(I)

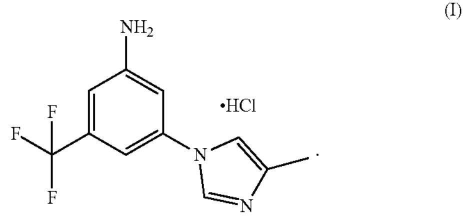 [SMILES: Cc1cn(-c2cc(N)cc(C(F)(F)F)c2)cn1 ; Cl]

In another preferred embodiment, the X-ray powder diffraction pattern of the crystal form A further has 2θ value characteristic peaks at of 6.29±0.2°, 18.93±0.2°, 20.55±0.2°, 29.28±0.2°, 31.7±0.2°.

In another preferred embodiment, the X-ray powder diffraction pattern of the crystal form A is substantially as shown in FIG. 1.

In another preferred embodiment, the crystal form A starts to decompose when heated to 226±3° C.

In another preferred embodiment, the thermogravimetric analysis chart of the crystal form A is substantially as shown in FIG. 2.

In another preferred embodiment, the crystal form A is an anhydrous substance, whose moisture content is less than 0.50%.

In another preferred embodiment, the moisture content of the crystal form A is ≤0.3%; preferably, is ≤0.25%.

In the second aspect of the present invention, a method for preparing the crystal form A described in the first aspect is provided, which comprises the following steps:

a) mixing 3-(4-methyl-1H-imidazol-1-yl)-5-trifluoromethylaniline free base with hydrochloric acid in an organic solvent;

b) cooling and stirring to afford a suspension;

c) filtering to collect the solid;

d) the obtained solids are dried at 50-80° C. under 10-20 mmHg until the moisture content <0.5% to afford the crystal form A of the compound of formula (I).

In another preferred embodiment, in step (a), the temperature of mixing is 20-80° C.; preferably, is 25-30° C. or 50-60° C.

In another preferred embodiment, the mixture liquid obtained by mixing in step (a) is a clear liquid.

In another preferred embodiment, in step (b), the cooling is slowly cooling to −25-25° C.

In another preferred embodiment, in step (b), the solid is precipitated at 10-50° C. (preferably 15-20° C. or 40-45° C.) during the cooling process.

In another preferred embodiment, the time of stirring is 1 to 10 hours.

In another preferred embodiment, in step (c), after filtering, further comprises rinsing the filter cake with acetone or toluene.

In another preferred embodiment, in step (d), the moisture content is ≤0.25%.

In another preferred embodiment, the organic solvent is one or two selected from methanol, toluene, and acetone.

In another preferred embodiment, the hydrochloric acid is 36%-38% hydrochloric acid, and the amount of hydrochloric acid is 1.0-1.2 eq.

In another preferred embodiment, the amount of hydrochloric acid is 1.1 eq.

The third aspect of the present invention provides a method for synthesizing nilotinib, including the following steps:

(1) dissolve a compound of formula (V) in an organic solvent, and adding a chlorinating reagent to form a mixture containing the compound of formula (IV);

(2) to the mixture containing the compound of formula (IV) obtained in step (1), adding the compound of formula (I) to react, and after the reaction completed, adjusting the pH value of the reaction solution to 7-14 (preferably, 7-12), thereby forming a compound of formula (II);

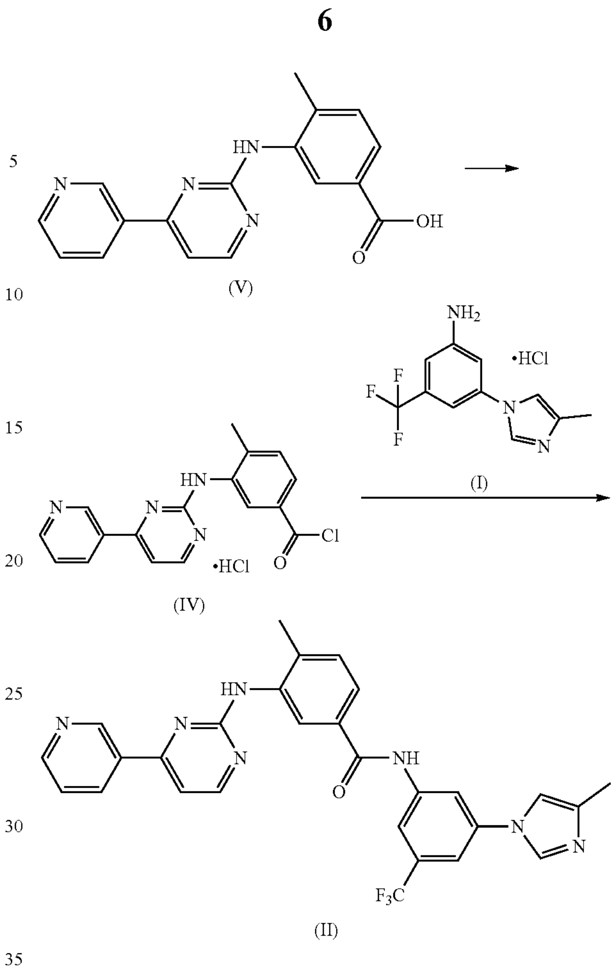

wherein the X-ray powder diffraction pattern of the compound of formula (I) has 2θ value characteristic peaks at 8.43±0.2°, 12.59±0.2°, 16.95±0.2°, 22.46±0.2°, 25.76±0.2°, 26.48±0.2°.

In another preferred embodiment, the preparation method includes one or more following features:

(1) the chlorinating reagent is selected from thionyl chloride, oxalyl chloride, phosphorus oxychloride;

(2) the organic solvent is N-methylpyrrolidone;

(3) the temperature for adding the chlorinating reagent is 0-80° C.;

(4) the pH value is 8-14, preferably, is 8-10, and more preferably, is 8-9 or 9-10.

In another preferred embodiment, the temperature for adding the chlorinating reagent is 25-50° C.

In another preferred embodiment, in step (2), after adjusting the pH value of the reaction solution, further comprise steps: cooling the reaction solution to 25-30° C., stirring, filtering, washing the filter cake, and drying the filter cake.

It should be understood that within the scope of the present invention, the above technical features of the present invention and the technical features specifically described in the following (e.g., embodiments) can be combined with each other, thereby forming a new or preferred technical solution. Due to space limitations, it will not be repeated herein.

DETAILED DESCRIPTION OF THE INVENTION

Figure 1:
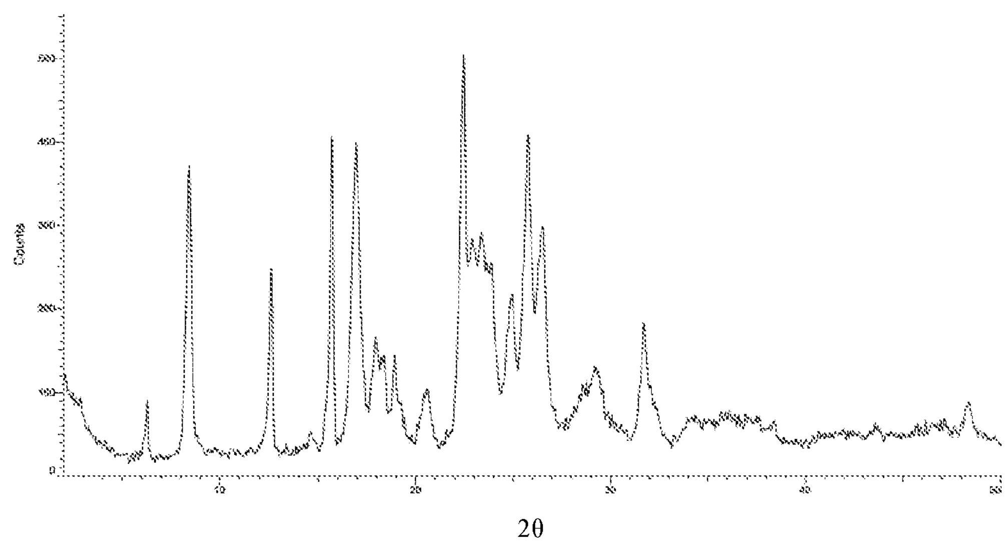
FIG. 1 shows the X-ray powder diffraction pattern of the crystal form A of the monohydrochloride anhydrous substance of 3-(4-methyl-1H-imidazol-1-yl)-5-trifluoromethylaniline.

After extensive and in-depth research, the inventors unexpectedly discovered that niloanime can be used in the synthesis of nilotinib compound in the form of monohydrochloride anhydrous substance, and there is no need to free the hydrochloride form of niloanime during the preparation process. During the study of the hydrochloride formation and crystallization of niloanime in specific organic solvents, it was found that the wet products obtained by filtration present in the form of hydrate or solvate, and have different crystal forms. By means of dehydration by heated under vacuum, the wet products would go through crystal transformation to hydrochloride anhydrous substance, which is of good stability and valuable for industrial use. The present invention was completed on this basis.

Experimental methods (such as X-ray powder diffraction pattern, thermogravimetric analysis pattern, stability test, etc.) used in the present invention are conventional technical means in the art and can be performed with conventional methods.

In the present invention, the term "hydrochloride of niloamine", "compound of formula (I)", or "3-(4-methyl-1H-imidazol-1-yl)-5-trifluoromethylaniline monohydrochloride" can be used interchangeably.

(I)

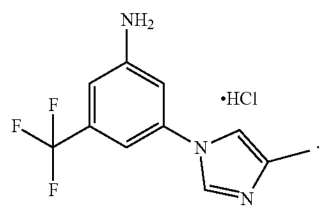

The present invention provides a crystal form A of a compound of formula (I).

The present invention provides a method for preparing the crystal form A of the compound of formula (I), comprising the following steps:

a) mixing 3-(4-methyl-1H-imidazol-1-yl)-5-trifluoromethylaniline free base with hydrochloric acid in an organic solvent;

b) cooling and stirring to afford a suspension;

c) filtering to collect the solid;

d) the obtained solids are dried at 50-80° C. under 10-20 mmHg until the moisture content <0.5% to afford the crystal form A of the compound of formula (I).

In another preferred embodiment, the method may comprise the following steps:

a) dissolving 3-(4-methyl-1H-imidazol-1-yl)-5-trifluoromethylaniline free base in the organic solvent till the solution is clear, and then mixing with hydrochloric acid;

b) cooling and stirring to afford a suspension;

c) filtering to collect the solid;

d) the obtained solids are dried at 50-80° C. under 10-20 mmHg until the moisture content <0.5% to afford the crystal form A of the compound of formula (I).

In another preferred embodiment, in step (a), the temperature of mixing is 20-80° C.; preferably, is 25-30° C. or 50-60° C.

In another preferred embodiment, in step (b), the cooling is slowly cooling to −25-25° C.

In another preferred embodiment, in step (b), the solid is precipitated at 10-50° C. (preferably 15-20° C. or 40-45° C.) during the cooling process.

In another preferred embodiment, the time of stirring is 1 to 10 hours.

In another preferred embodiment, in step (c), after filtering, further comprises rinsing the filter cake with acetone or toluene.

In another preferred embodiment, in step (d), the moisture content is ≤0.25%.

In another preferred embodiment, the organic solvent is one or two selected from methanol, toluene, and acetone.

In another preferred embodiment, the hydrochloric acid is 36%-38% hydrochloric acid, and the amount of hydrochloric acid is 1.0-1.2 eq, preferably 1.1 e.q.

The main advantages of the invention are:

(1) The present invention provides niloamine hydrochloride crystal form A and the preparation method thereof.

(2) Compared with the prior art, niloanime hydrochloride crystal form A provided by the present invention is anhydrous substance, which has better stability and purity, and can be directly used for the preparation of nilotinib.

(3) The present invention provides a method for preparing nilotinib, which uses niloamine hydrochloride anhydrous substance (crystal form A) to directly perform condensation reaction. The method avoids the cumbersome operation including recrystallization after freeing niloamine hydrochloride, improves the yield of the product and efficiency of production, thus reducing the production cost, which has important industrial application value.

The present invention was further described hereafter in combination with specific embodiments. It should be understood that these examples are only used to illustrate the and not to limit the scope of the invention. The experimental methods without specific conditions in the following examples generally follow the conventional conditions or the conditions suggested by the manufacturer. Unless indicated otherwise, parts and percentage are calculated by weight.

The experimental materials and reagents used in the following examples can be obtained from commercial sources unless otherwise specified.

The X-ray powder diffraction pattern described in the present invention was collected from the Bruker D2 Phaser X-ray powder diffractometer, and the parameters of instrument are as follows:

Ray: monochromatic Cu-Kα rays (λ=1.5418)

Scanning method: θ/2θ

Scanning range: 2-50°

Voltage: 30 KV

Current: 10 mA

The thermogravimetric analysis pattern described in the present invention was collected from the TGA55-type thermogravimetric analyzer, TA Instruments, and the parameters of instrument are as follows:

Heating rate: 10.0° C./min

Temperature range: 30-320° C.

Nitrogen flow rate: 40 mL/min

The moisture described in the present invention is collected from the 870 type Karl-Fisher Titrator Coulometric Moisture Titrator, Metrohm Company.

Example 1: Preparation of Niloamine Hydrochloride 3-(4-methyl-1H-imidazol-1-yl)-5-trifluoromethylaniline free base (12.0 g, 50 mmol, purity 88.5%) was dissolved in the mixed solvent of methanol (54 mL) and acetone (270 mL), stirred till dissolved to clear. Concentrated hydrochloric acid (5.43 g, 55 mmol) was added at 25-30° C., then cooled down slowly. The solid was precipitated at about 15-20° C., and cooled to −10~−5° C. to stir for 2 hours. The mixture was filtered, and the filter cake was rinsed with cold acetone, while the wet product was dried to constant weight at 80° C. under 10-20 mmHg to afford 11 g solid of the hydrochloride crystal form A, of which the moisture was 0.19%, and purity was 99.69%. The X-ray powder diffraction pattern thereof was shown in FIG. 1; and the thermogravimetric analysis chart thereof was shown in FIG. 2.

Figure 2:
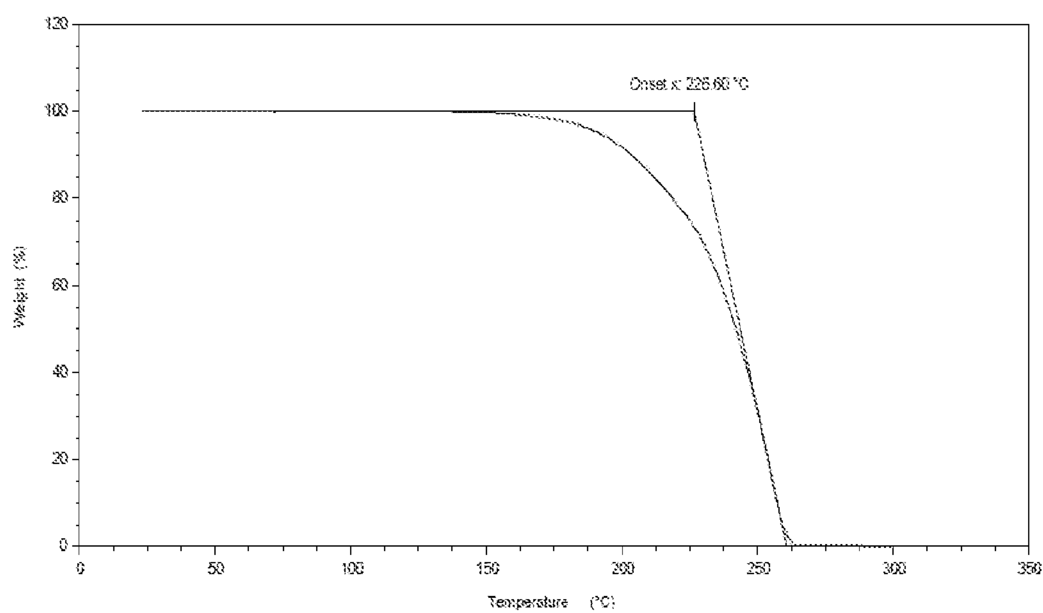
FIG. 2 shows the thermogravimetric analysis chart of the crystal form A of the monohydrochloride anhydrous substance of 3-(4-methyl-1H-imidazol-1-yl)-5-trifluoromethylaniline.

Example 2: Preparation of Niloamine Hydrochloride 3-(4-methyl-1H-imidazol-1-yl)-5-trifluoromethylaniline free base (12.0 g, 50 mmol, purity 88.5%) was dissolved in the mixed solvent of toluene (54 mL) and acetone (270 mL), heated to 50-60° C. under stirring. Concentrated hydrochloric acid (5.43 g, 55 mmol) was added and cooled down slowly, and solid was precipitated at about 40° C. The mixture was stirred for 2 hours after cooled to 15-20° C., filtered, and the filter cake was rinsed with cold acetone, while the wet product was dried to constant weight at 70° C. under 10-20 mmHg to afford 11.5 g solid of the hydrochloride crystal form A, of which the moisture was 0.23%, and purity was 99.76%. The X-ray powder diffraction pattern thereof was substantially as shown in FIG. 1; and the thermogravimetric analysis chart thereof was substantially as shown in FIG. 2.

Example 3: Preparation of Niloamine Hydrochloride 3-(4-methyl-1H-imidazol-1-yl)-5-trifluoromethylaniline free base (80.0 g, 0.33 mol, purity 88.5%) was dissolved in the mixed solvent of methanol (0.32 L) and toluene (1.28 L), heated to 50-60° C. under stirring till dissolved to clear. Concentrated hydrochloric acid (32 g, 0.33 mmol) was added, and the mixture was cooled down slowly. Solid was precipitated at about 45° C., and after cooled to 0-5° C. to stir for 3 hours. The mixture was filtered, and the filter cake was rinsed with cold toluene. The wet product was dried to constant weight at 65-70° C. under 10-20 mmHg to obtain 93 g solid of the hydrochloride crystal form A, of which the moisture was 0.18%, and a purity of 99.84%. The X-ray powder diffraction pattern thereof was substantially as shown in FIG. 1; and the thermogravimetric analysis chart thereof was substantially as shown in FIG. 2.

It can be seen that none of the crystal form A prepared according to the present invention was less than 99.50% purity.

Example 4: Preparation of Nilotinib

To a reaction flask 4-methyl-3-[[4-(3-pyridinyl)-2-pyrimidinyl]amino]benzoic acid (10 g, 32.64 mmol) and dried N-methylpyrrolidone (50 mL) were added and heated to 45-50° C. Thionyl chloride (7.77 g, 65.2 mmol) was added and stirred for 2 h. Then 3-(4-methyl-1H-imidazol-1-yl)-5-trifluoromethylaniline monohydrochloride (10 g, 35.90 mmol, moisture 0.19%) obtained in Example 1 was added and continue to stir for 2 h. The mixture was adjusted to pH=8-9 by adding 2M sodium hydroxide aqueous solution dropwise, then cooled to 25-30° C. and stirred for 2 h, filtered and the filter cake was washed with water. The filter cake was dried to obtain 14.7 g of yellow solid, of which the yield was 85% and the purity was 99.83%.

It can be seen that the preparation of nilotinib using the crystal form A of niloanime hydrochloride prepared according to the present invention is very easy to operate, while freeing the hydrochloride into base form is not necessary. The method obtained nilotinib in good yield (more than 75%) and high purity (more than 99%), which substantially can be directly used in preparing medicines, thus greatly simplifying the production steps and reducing production costs.

All documents mentioned in the present invention are cited as references in this application, just as each document is individually cited as a reference. In addition, it should be understood that, after reading the above teaching content of the present invention, those skilled in the art can make various changes or modifications to the present invention, and these equivalent forms also fall within the scope defined by the appended claims of the present application.

The invention claimed is:

1. A crystal form A of a compound of formula (I), wherein the X-ray powder diffraction pattern thereof has 2θvalue characteristic peaks at of 8.43±0.2°, 12.59±0.2°, 16.95±0.2°, 22.46±0.2°, 25.76±0.2°, 26.48±0.2°;

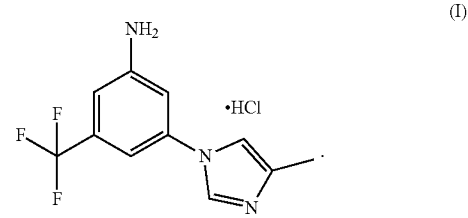 [SMILES: Cc1cn(-c2cc(N)cc(C(F)(F)F)c2)cn1 ; Cl]

2. The crystal form A of claim 1, wherein the X-ray powder diffraction pattern thereof further has 2θvalue characteristic peaks at of 6.29±0.2°, 18.93±0.2°, 20.55±0.2°, 29.28±0.2°, 31.7±0.2°.

3. The crystal form A of claim 1, wherein the X-ray powder diffraction pattern of the crystal form A is substantially as shown in FIG. 1.

4. The crystal form A of claim 1, wherein the crystal form A starts to decompose when heated to 226±3° C.

5. The crystal form A of claim 1, wherein the crystal form A is an anhydrate, and its moisture content is less than 0.50%.

6. A method for preparing the crystal form A of claim 1, wherein comprising the following steps:

a) 3-(4-methyl-1H-imidazol-1-yl)-5-trifluoromethylaniline free base is mixed with hydrochloric acid in an organic solvent;

b) cooling and stirring to afford a suspension;

c) filtering to collect the solid;

d) the obtained solids are dried at 50-80° C. under 10-20 mmHg until the moisture content <0.5% to afford the crystal form A of the compound of formula (I).

7. The preparation method of claim 6, wherein the organic solvent is one or two selected from methanol, toluene, acetone.

8. The preparation method of claim 6, wherein the hydrochloric acid is 36%-38% hydrochloric acid, and the amount of hydrochloric acid is 1.0-1.2 eq.

9. A method for synthesizing nilotinib, characterized in that it comprises the following steps:

(1) dissolve a compound of formula (V) in an organic solvent, and adding a chlorinating reagent to form a mixture containing the compound of formula (IV);

(2) to the mixture containing the compound of formula (IV) obtained in step (1) adding the compound of formula (I) to react, and after the reaction completed, adjusting the pH value of the reaction solution to 7-14, thereby forming a compound of formula (II);

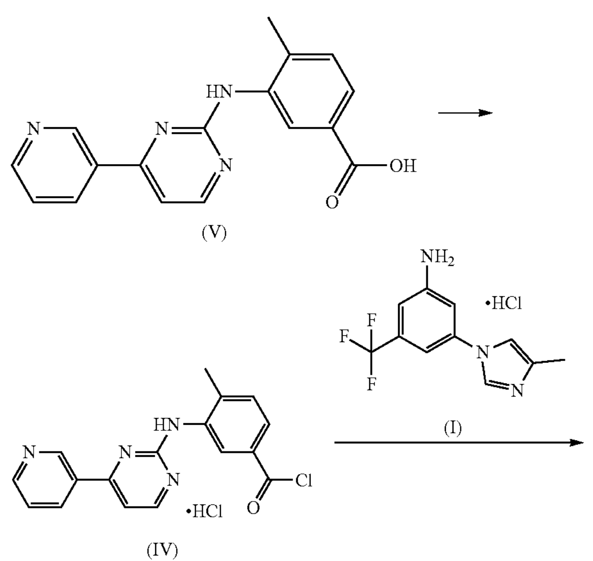

-continued

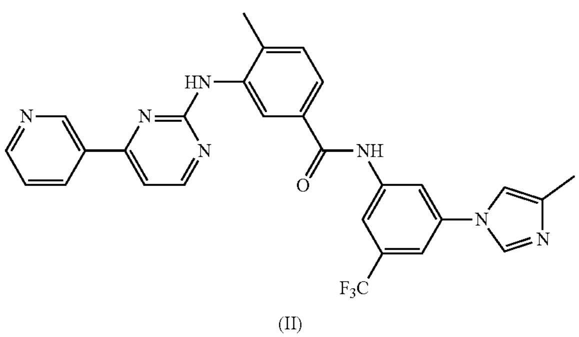

wherein the compound of formula (I) is a crystal form A of claim 1, and the X-ray powder diffraction pattern thereof has 2θvalue characteristic peaks at 8.43±0.2°, 12.59±0.2°, 16.95±0.2°, 22.46±0.2°, 25.76±0.2°, 26.48±0.2°.

10. The method of claim 9, wherein the preparation method includes one or more following features:

(1) the chlorinating reagent is selected from thionyl chloride, oxalyl chloride, phosphorus oxychloride;

(2) the organic solvent is N-methylpyrrolidone;

(3) the temperature for adding the chlorinating reagent is 0-80° C.;

(4) The pH value is 8-14.

* * * * *